United States Patent [19]

Schaldach et al.

[11] Patent Number: 5,354,320
[45] Date of Patent: Oct. 11, 1994

[54] NEUROSTIMULATOR FOR PRODUCTION OF PERIODIC STIMULATION PULSES

[75] Inventors: Max Schaldach, Erlangen; Helmut Hutten, Mainz, both of Fed. Rep. of Germany

[73] Assignee: Biotronik Mess- Und Therapiegerate GmbH & Co., Ingenieurburo Berlin, Berlin, Fed. Rep. of Germany

[21] Appl. No.: 943,250

[22] Filed: Sep. 14, 1992

[30] Foreign Application Priority Data

Sep. 12, 1991 [DE] Fed. Rep. of Germany ....... 4130597

[51] Int. Cl.$^5$ .............................................. A61N 1/34
[52] U.S. Cl. .......................................... 607/46; 607/72
[58] Field of Search ............... 128/421, 419 R, 419 C; 600/26, 27; 607/68, 72, 73, 46, 2

[56] References Cited

U.S. PATENT DOCUMENTS

| | | | |
|---|---|---|---|
| 4,210,151 | 7/1980 | Keller, Jr. | 128/421 |
| 4,784,142 | 11/1988 | Liss et al. | 128/421 |
| 4,793,353 | 12/1988 | Borkan | 128/421 |
| 4,913,148 | 4/1990 | Diethelm | 128/421 |
| 5,058,584 | 10/1991 | Bourgeois | 128/421 |
| 5,063,929 | 11/1991 | Bartelt et al. | 128/421 |
| 5,084,007 | 1/1992 | Malin et al. | 128/421 |

FOREIGN PATENT DOCUMENTS

| | | |
|---|---|---|
| 0036742 | 9/1981 | European Pat. Off. . |
| 0111229 | 6/1984 | European Pat. Off. . |
| 3042437 | 6/1982 | Fed. Rep. of Germany . |
| 2336145 | 7/1977 | France . |
| 2537441 | 6/1984 | France . |

OTHER PUBLICATIONS

Biomedizinische Technik, Band 35, Erganzungsband 2, 1990 M. Shaldach et al., "Implantierbarer Neurostimulator mit programmierbarer Logik", Seiten 138-140.

Primary Examiner—William E. Kamm
Assistant Examiner—Kennedy J. Schaetzle
Attorney, Agent, or Firm—Spencer, Frank & Schneider

[57] ABSTRACT

A neurostimulator for generating stimulation pulses for the central or peripheral nervous system, particularly against pain in the region of the spinal cord includes a control circuit for generating stimulation pulses with a pulse generator whose output is connected with stimulation electrodes. The stimulation pulses are generated at periodic intervals with an activity period corresponding essentially to an effective duration corresponding to a biological half-lifetime of a body's own active substances. The control circuit creates a respective rest period corresponding to a time required by the body's own active substances to regenerate themselves for a corresponding activity period.

11 Claims, 3 Drawing Sheets

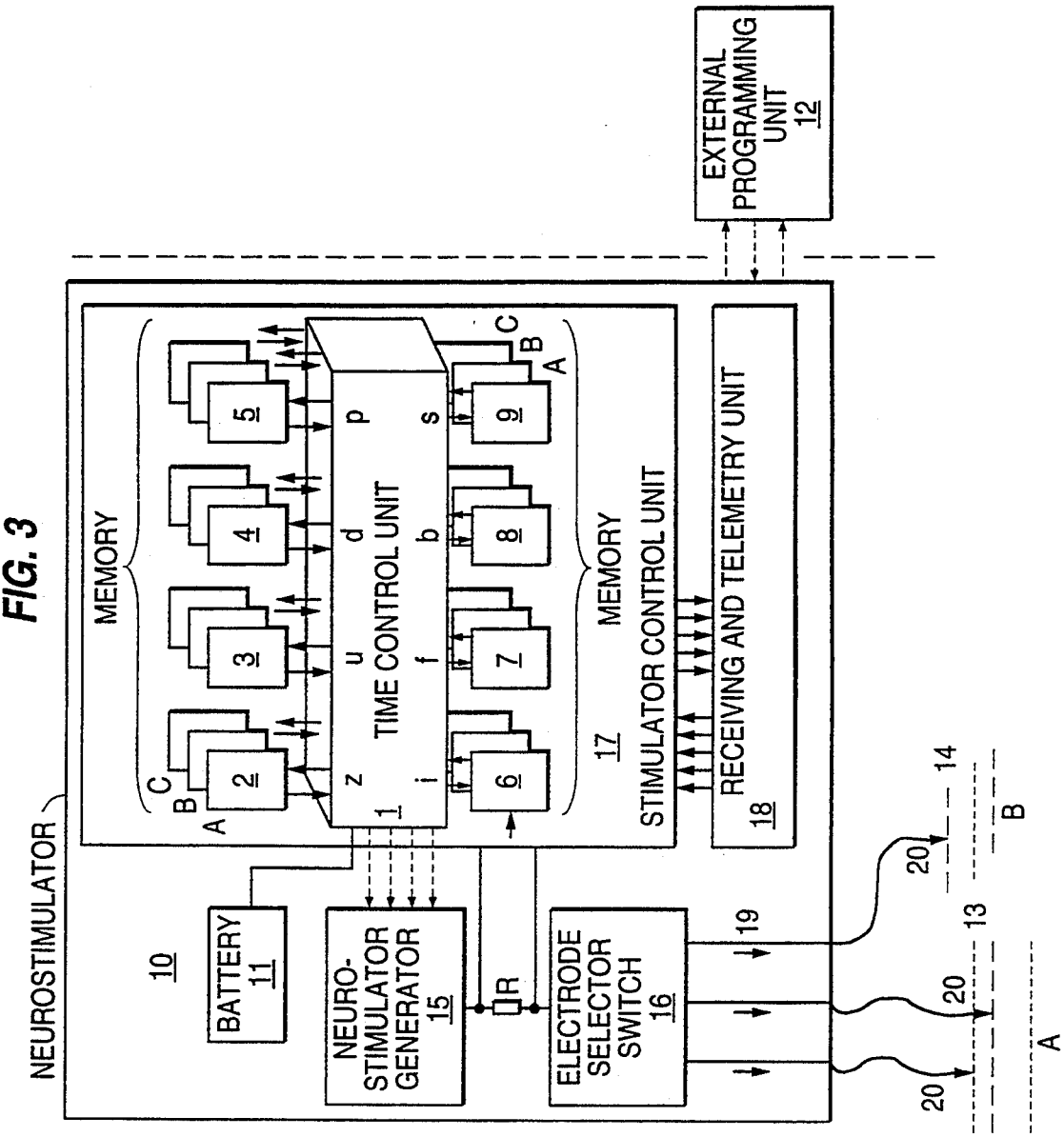

NEUROSTIMULATOR FOR PRODUCTION OF PERIODIC STIMULATION PULSES

SPECIFICATION

The invention relates to a neurostimulator.

Treatment with a neurostimulator, particularly if drug therapy is insufficient and surgical intervention is connected with a high risk, brings about results in patients who, due to impairments in peripheral blood circulation, suffer from night pain. Reflex generated pain to be eliminated with spinal cord stimulation occurs in the so-called Head's zones which receive their sensory fibers from the same spinal chord segment as the diseased organs. Electrostimulation is to be felt in the Head's zones. Stimulation of nerve functions is employed not only for the suppression of pain but also for the stimulation of increased blood circulation in the diseased organs.

One problem of implanted devices is the gradually exhausted energy supply. Even with long-term batteries, such devices are able to operate with pulsed or burst-shaped stimulation only for so long. Thus, the prior art devices are unable to operate without an external energy source.

A neurostimulator is known in the art which includes an external transmitter and an implantable receiver as well as an antenna that can be glued to the skin. During the post-operative phase, pain is reduced either by continuous wave stimulation or by stimulation bursts, with the amplitude and the duration of the stimulation pulses being adjustable through the transmitter in the patient device. For example, pain reduction decreases gradually as the patient becomes used to the device so that the dosage must be increased. It is also customary for the patient to decide how long the pulses are to continue. Thus, night pain again and again interrupts the patient's rest and it would thus be desirable for stimulation to take place automatically, without interference and overdoses.

An implantable neurostimulator is known which is equipped with a programmable logic unit disposed within the implantable receiver to generate stimulation pulses and with an implantable multiple electrode. For stimulation, the neurostimulator cooperates with a device outside the patient's body which, at greater intervals, can selectively be brought in connection with a programming device (M. Schaldach, H. Hutten, J. Jirmann, U. Krainick, "Implantierbarer Neurostimulator mit programmierbarer Logik" (Implantable Neurostimulator Equipped With a Programmable Logic Unit), Biomedizinische Technik [Biomedical Technology] 35, Supplemental Volume 2, pages 138–140). The programming device changes all operating parameters which are then transferred by way of a suitable interface into the memory of the patient device.

When turned on, the patient device wirelessly transmits to the implant all individually adapted operating parameters —with the patient being able to vary only the amplitude and the duration of the stimulation pulse within certain limits—and additionally also the energy required for operation. The implant includes a circuit which generates a controlled supply voltage from the received carrier and operates with undervoltage detection. The implant includes a circuit for receiving, demodulating and converting the electrode selection word transmitted immediately before the stimulation pulse into an 8-bit data word which, after checking, is forwarded to the CMOS electrode selector switch. After demodulation and amplification in an analog circuit, the received stimulation pulse is output by the selected CMOS electrode selector switch to the predetermined electrode while an additional current measuring resistor measures the stimulation current and sends it, amplified by way of a measuring amplifier, to a passive telemetry circuit.

Counterproductive to the effective stimulation by the stimulation pulses is that the arrangement of the antenna does not ensure sufficient coupling of the transmitter during movements, particularly during a change in the patient's position during sleep. Rather, it is necessary to have a report from the implant to the patient device (passive telemetry by way of periodic detuning of the energy transmission circuit) requesting the patient to maintain the necessary conditions.

In connection with the implementation of electrostimulation it is already known to support the latter by chemical agents. These active substances are usually also supplied to the patient's body by way of injections or as medication supplied in the form of pills and the like or also externally, but it is difficult to locally concentrate the effect of such medications. To this end, special patches are known which dispense dosages of long-term medications. The realizable effects, however, are not suitable to basically reduce the energy consumption of the neurostimulator.

SUMMARY OF THE INVENTION

It is the object of the invention to improve the effect of an electronic circuit of the above-mentioned type with low energy consumption.

Based on the known general sequence of the operation and function of nerve cells, it is possible to exert a controlling influence on this sequence in that electrostimulation of the central or peripheral nervous system causes active chemical agents to be released within local limits.

The invention is based on the realization that, in contrast to the conduction of electrical charges (conduction of electrical excitations), nerve stimuli in the nervous system are also transmitted chemically by means of chemical transmitting agents (neurotransmitters). Neurotransmitters are synthesized at the ends of presynaptic fibers and are there stored in vesicles. If these neurotransmitters are released upon the arrival of an action potential, they quickly diffuse through the synaptic gap and produce a change in potential across the postsynaptic membrane, thus controlling the electrical conduction and excitation. The preganglionic neurons of the parasympathetic nerve and of the sympathetic nerve are, for example, cholinergic; the post-ganglionic neurons of the parasympathetic nerve are also cholinergic but the post-ganglionic neurons of the sympathetic nerve are noradrenergic. The inactivation is effected partly by chemical agents (for the case of acetylcholine by cholinesterase) partly by reintroduction into the vesicles (for the case of noradrenaline).

In this connection, it has been found to be advantageous that neurotransmitters act directly on the nerve function and excite them in such a way that, in spite of a reduction of the electrical energy, they react with preference to electrostimulation. During directed stimulation it appears that chemical agents are released that have a longer biological half-lifetime and block the path of the pain in the spinal cord. The energy consumption of the implanted neurostimulator is reduced by a time control unit which influences the height of the pulse amplitudes and/or the time intervals between the pulses and/or the pulse widths and the spacing between the bursts as well as the time and duration of the stimulation.

The time control unit of the electronic circuit of the neurostimulator is here adapted to the respective specific biological half-lifetime of these chemical agents so that their effect can be maintained quasi uniformly over a long period of time with a minimum of energy consumption.

BRIEF DESCRIPTION OF THE DRAWINGS

Advantageous features of the invention will be described in greater detail below together with a description of the preferred embodiment of the invention and the drawing figures, in which:

FIG. 3 is a block circuit diagram of a further embodiment of a circuit for a neurostimulator including a communication device.

DETAILED DESCRIPTION OF THE PREFERRED EMBODIMENTS

Figure 1:
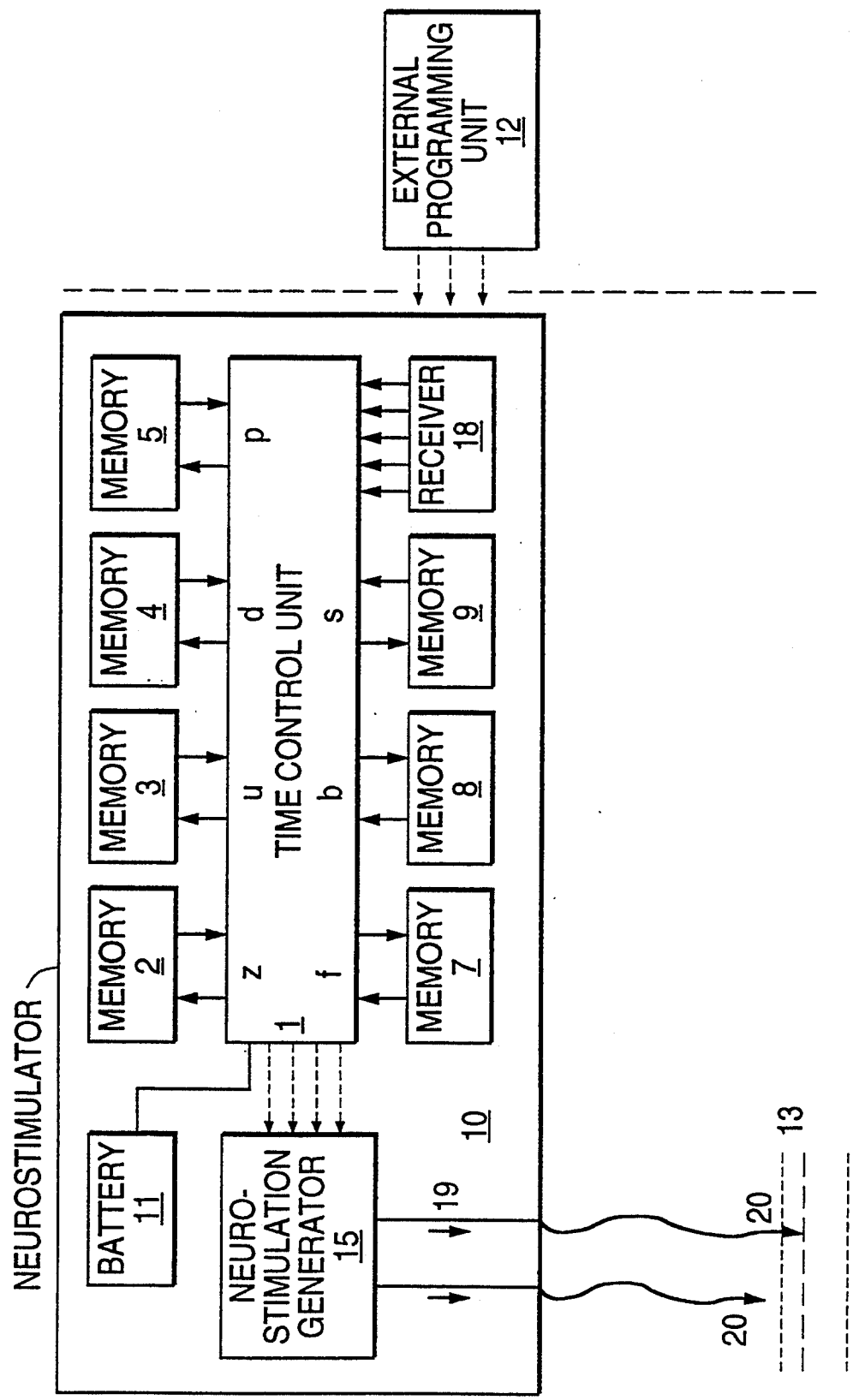
FIG. 1 is a block circuit diagram of an electronic circuit for an embodiment of the neurostimulator according to the invention.

FIG. 1 is a block circuit diagram of an electronic circuit 10 of an embodiment of the neurostimulator according to the invention. It includes a time control unit 1, to which are connected a memory 2 for the value of the biological half-lifetime z, a memory 3 for the value of the pulse amplitude u, a memory 4 for the value of the duration d of an individual pulse, a memory 5 for the value of the pause between pulse packets p, a memory 7 for the frequency value f, a memory 8 for the value of the burst width b and a memory 9 for the values of the operating mode s. Corresponding to the value of the required dosage, values s are given in a memory 9 for the polarity of the pulse or for a change of polarity and for a soft start. By way of time control unit 1, the sequence and a neurostimulation generator 15 are controlled in such a manner that less energy is required if the neurons are excited locally by neurostimulation. By adapting the repetition rate of the stimulation to the half-lifetime of the body's own chemical agents, the neurotransmitters, the interval between the electrostimulation phases can be increased and thus energy can be saved.

For the purpose of programming, time control unit 1 may be charged with signals by way of a receiver 18 and permits a programmed influence on the time intervals between the electrostimulation phases corresponding to the biological half-lifetime of the released chemical agents of the body as well as all other parameters. The programming is effected at selectable intervals by means of an external programming unit 12.

Figure 2:
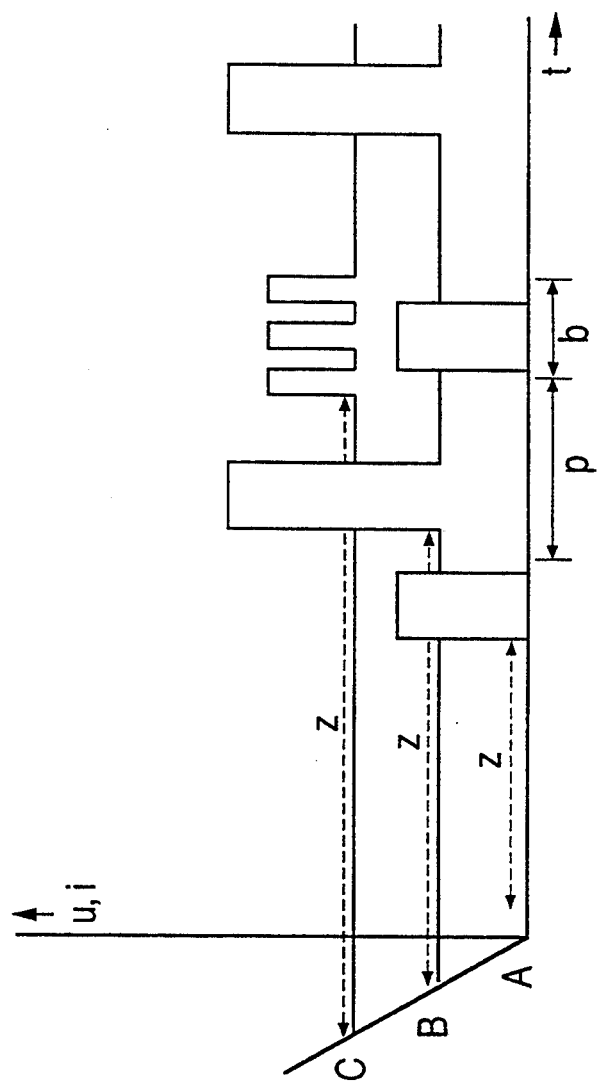
FIG. 2 is an associated stimulation diagram.

FIG. 2 shows a typical stimulation diagram of a circuit according to FIG. 1. It is clearly visible that the time phases of the electrostimulation are a function of the biological half-lifetime while, the stimulation energy to be expended, and thus the dosage of the released chemical agents, is of a different magnitude at different locations. Not shown is how the individual zones can be stimulated in an alternating succession.

In the modification of the invention shown in FIG. 3 it is also possible, if suitable programming is provided, to change the local dosage of the chemical agents by way of an expanded external programming and monitoring unit 12 and by way of the given spacing between the electrostimulation phases as a function of the biological half-lifetime, and also to signal the dosage quantity value required, thus enabling the physician to monitor the required dosage quantity. For this purpose a stimulator control unit 17 is employed. It is connected by way of measuring lines with a current measuring resistor R in leads 19 that lead to electrodes 20. The thus measured momentary current value i is transferred to and stored in a memory 6. The stimulator control unit 17 continuously determines the current i by way of the current measuring resistor R and from it the dosage quantity value M or the tissue resistance Rg at the location where the electrodes are placed and, in connection with the latter, the momentary value z of the biological half-lifetime which, if required, can be read out from or predetermined by the external programming and monitoring unit 12. Thus, it is possible to detect changes in this respect and to evaluate them for renewed programming. The time control unit 1 and the associated memories 2 to 9 are grouped in planes A to C according to the locations of electrostimulation and treatment regions.

In an advantageous manner, time control unit 1 is configured, as far as its software is concerned, by a stimulator control 7 included in a microcomputer.

If multiple electrodes are implanted, the connection of the respective electrode 20 is effected by way of an electrode selector switch 16. The individual sections 13, 14 of the spinal cord may be stimulated individually one at a time or in succession. The effect then lasts longer in body regions A, B, C, etc.

The charge status of battery 11 is also constantly monitored by stimulator control unit 17 which also controls the spacing (pauses) between the pulse groups in which neurostimulator generator 15 emits bursts of pulses to at least one electrode 20 per stimulation location A, B and C, respectively. In these pauses p between pulse packets, the voltage of battery 11 is measured, which is then only under a minimum load (only stimulator control unit 17). In a known manner this permits a determination of the charge status which is stored intermediately in a further memory (not shown) and can be read out from there if required. The housing of the implantable neurostimulator 10 may be configured as a counter-electrode so that only one lead 19 per electrode 20 is required. The polarity of the pulses can be programmed and may change alternatingly, for which purpose memory 9 is connected to time control unit 1. The latter also controls a defined rise time for the pulses at the beginning and end of the pulse packet.

Although external programming and monitoring units 12 are known which are able to communicate with the implanted device and can be connected with a receiving and telemetry unit 18, the implant in the past has not operated autonomously but was always in communication with the patient device and required an external energy supply.

Additionally, it is now possible to automatically react to a changing stimulation threshold which is determined by time control unit 1 by way of a measurement of the tissue resistance Rg and the dosage quantity value M. The external programming and monitoring unit (12) can be connected with the receiving and telemetry unit (18) of the neurostimulator (10) at any desired time. In an advantageous manner, communication is effected by way of laser diodes and an at least partially light transmitting housing if the external programming and monitoring unit (12) is placed onto the skin under which the implant is disposed. During the other time, the implanted neurostimulator operates independently and, because of its battery 11, autonomously. Thus, the dependence on a transmitter-receiver coupling and the susceptibility to the patient's movements are eliminated.

The neurostimulation generator 15 to which electrodes 20 are connected at the one end of a line 19 acts within local limits at the other end of line 19 so that chemical agents are discharged that have a defined specific half-lifetime and produce a longer lasting effect in the Head's zones corresponding to the electrostimulation. Patient specific biorhythms can here be considered so that during a programmed time period, for example during an hour, stimulation bursts occur once for five minutes, thus optimizing the effect and making it last even longer.

If the coupling is made on a daily cycle, the pulse dosage during the night is reduced.

The invention is not limited in its embodiments to the above-described preferred embodiment. Rather, a number of variations are conceivable which take advantage of the described solution even for basically different configurations.

We claim:

1. A neurostimulator for generating stimulation pulses for the central or peripheral nervous system, particularly against pain in the region of the spinal cord, comprising:
   stimulation electrodes and
   a control circuit including pulse generator means for generating stimulation pulses to the stimulation electrodes at periodic intervals with an activity period corresponding essentially to an effective duration corresponding to a biological half-lifetime of a body's own active substances and means for creating a respective rest period, the respective rest period corresponding to a time required by the body's own active substances to regenerate themselves for a corresponding activity period.

2. A neurostimulator according to claim 1, further comprising programming means for changing a duration of the intervals and/or a ratio of the activity period to interval duration.

3. A neurostimulator according to claim 2, wherein the programming of the interval duration and/or the ratio of activity period to interval duration can be varied by said programming means within a 24-hour cycle.

4. A neurostimulator according to claim 1, further comprising an internal energy source.

5. A neurostimulator according to claim 1, further comprising programmable selector circuit means for establishing electrical connections between the output of the pulse generator and one or a plurality of said stimulation electrodes in different combinations or sequences.

6. A neurostimulator according to claim 1, further comprising means for effecting burst stimulation during the activity period.

7. A neurostimulator according to claim 2, wherein pulse amplitude is programmable by said programming means.

8. A neurostimulator according to claim 2, wherein, at the beginning of stimulation, said programming means programs said control circuit with a value of the biological half-lifetime and a dosage quantity value.

9. A neurostimulator according to claim 1, wherein said programming means comprises an external programming and monitoring unit including a receiving and telemetry unit.

10. A neurostimulator according to claim 9, wherein said receiving and telemetry unit further comprises means for effecting passive telemetry whereby communication is effected by means of passive telemetry.

11. A neurostimulator according to claim 1, wherein said control circuit further includes means for measuring tissue resistance and means for automatically reacting to a changing stimulation threshold determined by said means for measuring tissue resistance and from a dosage quantity value, whereby said control circuit adapts itself to a patient specific biorhythm.

* * * * *